United States Patent [19]

Browne

[11] Patent Number: 5,015,239

[45] Date of Patent: May 14, 1991

[54] SHEATH INTRODUCER APPARATUS

[76] Inventor: Kevin F. Browne, 1030 Lake Hollilngsworth Dr., Lakeland, Fla. 33803

[21] Appl. No.: 327,089

[22] Filed: Mar. 22, 1989

[51] Int. Cl.$^5$ .............................................. A61M 5/178
[52] U.S. Cl. .................................. 604/166; 604/280; 604/164
[58] Field of Search .................................. 604/51–53, 604/164–170, 264, 280–283; 128/343

[56] References Cited

U.S. PATENT DOCUMENTS

| 3,082,769 | 3/1963 | Palmer | 604/166 |
| 3,788,318 | 1/1974 | Kim et al. | 604/164 |
| 4,411,655 | 10/1983 | Schreck | 604/165 |
| 4,498,902 | 2/1985 | Ash et al. | 604/164 |
| 4,665,918 | 5/1987 | Garza et al. | 128/343 |

FOREIGN PATENT DOCUMENTS

| 0150281 | 8/1985 | European Pat. Off. | 604/166 |
| 0206553 | 12/1985 | European Pat. Off. | 604/280 |
| 3814618 | 2/1989 | Fed. Rep. of Germany | 604/164 |

Primary Examiner—C. Fred Rosenbaum
Assistant Examiner—Corrine Maglione
Attorney, Agent, or Firm—Dominik, Stein, Saccocio, Reese, Colitz & Van Der Wall

[57] ABSTRACT

A sheath introducer apparatus and method which includes a unique headed introducer/dilator that protects the leading edge or tip of the sheath from damage during insertion and which includes a sheath which is expandable along its longitudinal length.

11 Claims, 2 Drawing Sheets

SHEATH INTRODUCER APPARATUS

BACKGROUND OF THE INVENTION

1. Field of the Invention

This invention relates to devices for obtaining percutaneous access in intra-arterial and intravenous therapy in medicine. More particularly, this invention relates to intravascular sheaths and methods for percutaneous insertion of such sheaths.

2. Description of the Background Art

The use of intra-arterial and intravenous therapy in medicine has revolutionized therapy both in terms of administration of drugs and fluids and also the use of therapeutic devices placed in remote portions of the body from percutaneous access. Devices to obtain percutaneous access has traditionally involved metal or plastic sheaths which remained in dwelling after percutaneous puncture of the appropriate vessel through the skin. These devices could either be withdrawn after therapy was complete or left in dwelling for many days. The placement of the sheath is done by a skilled operator. The following describes three of the more common methods for sheath placement.

One of the older methods for placement of intravascular sheaths employs a sheath that is tightly wrapped over a steel needle. The needle is placed through the skin and into a vein. A sheath is then advanced over the needle into the vein. Once in place, the needle is withdrawn leaving the sheath in the desired position in the vein.

Another method also employs the use of a hypodermic needle to puncture the skin. The needle is then inserted into the desired vein. A plastic tube is inserted within the inner hollow core of the needle and advanced until the tube enters the vein. The needle is then withdrawn from the vein in the skin, leaving the tubing within the vein.

Finally, the third method for placement of intravascular sheaths is commonly known as the "Seldinger"'technique. As before, the Seldinger technique employs the use of a hypodermic needle to puncture the skin and enter the desired vein. A metal guide wire is inserted within the inner hollow core of the needle and then advanced through the needle into the vein. The needle is then removed. A hollow core introducer, usually made of plastic over which a sheath is tightly wrapped, is placed over the metal wire and advanced along the length of the wire to dilate the skin, vein wall and lumen of the vein and to "introduce" the sheath therein. The sheath is then slightly advanced over the introducer a the introducer and the metal guide wire are removed, leaving only the sheath within the vein.

Each of the methods for arterial catherization have enjoined various degrees of popularity; however disadvantages are associated with each. Specifically the second method referenced above in which a plastic tube is inserted within the hollow core of the needle, has the disastrous potential of inadvertently shearing off the plastic tube on the sharp edge of the needle. Thus, it is more common to utilize either the first or third methods referenced above in which the sheath is inserted over the needle or over a dilator/introducer. Unfortunately, both of these methods commonly present a problem of the sheath edge being caught by the subcutaneous tissue or the muscular tissue making up the arterial wall. Once the edge is caught, a kink is formed in the sheath, rendering further entry into the vein either impossible or at best difficult. Furthermore, the risk of injury or trauma to the vein is significantly increased.

Therefore, it is an object of this invention to provide an apparatus which overcomes the aforementioned inadequacies of the prior art devices and provides an improvement which is a significant contribution to the advancement of the sheath introducer art.

Another object of this invention is to provide a sheath introducer apparatus and method which minimizes risk of the sheath edge being caught by the subcutaneous tissue or the muscular tissue making up the arterial wall, thereby minimizing kinking or other damage to the sheath which in turn minimizes trauma of the subcutaneous tissues and arterial walls from a kinked sheath.

Another object of this invention is to provide a sheath introducer apparatus and method which does not employ the insertion of a tube within a hypodermic needle that could otherwise run the risk of shearing off the plastic tube on the sharp edge of the needle.

Another object of this invention is to provide a sheath introducer apparatus and method which allows more force to be applied to the introducer without damage to its sheath thereby making access through scarred tissue easier while minimizing damage to the sheath.

Another object of this invention is to provide a sheath introducer apparatus and method including a sheath which is expandable along its longitudinal length, allowing devices which are larger than the inner diameter of the collapsed sheath, to be utilized.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a sheath introducer apparatus and method which includes a unique headed introducer/dilator which protects the leading edge or tip of the sheath from damage during insertion and which includes a sheath which is expandable along its longitudinal length.

More particularly, the introducer includes a neck portion of a reduced diameter which defines the head of the introducer. An annular blind slot is formed longitudinally within the head about its circumference, with the opened end of the slot extending through the vertical wall between the inner section of the neck portion and the head. A thread is formed within the annular slot. The slot allows the tip of the sheath to be compressed to a reduced diameter and then inserted into the slot. Slight rotation of the sheath interlocks the tip of the sheath within the annular slot thereby interlocking the tip of the sheath within the head of the introducer.

During use, a metal guide wire is inserted through the subcutaneous tissue into the arterial vein as described above. After the needle is withdrawn, the proximal end of the guide wire is threaded through an axial hole formed within the introducer of the invention. The introducer, along with its sheath mounted and interlocked thereon as described above, is then advanced along the length of the guide wire through the subcutaneous tissue and into the arterial vein. Once positioned as desired, the sheath is slightly counter rotated in the opposite direction until its tip disengages from the annular slot formed within the head of the introducer. The sheath returns to its natural cylindrical design having an inner diameter equal to or slightly greater than the outer diameter of the introducer. The introducer and the guide wire may then be removed, leaving the sheath in the desired position within the arterial vein.

A primary feature of the invention is the uniquely designed, headed introducer which allows the tip of the sheath to be inserted within an annular slot therein. The protection of the tip of the sheath minimizes damage to the sheath while minimizing trauma to the arterial wall which may otherwise occur if the sheath was kinked or otherwise damaged. Moreover, the protection of the tip of the sheath allows greater force to be exerted on the introducer to force it through scarred tissue.

Another important feature of the invention is the expandability of the sheath which allows its tip to be slightly compressed to a reduced diameter for insertion within the annular slot in the head of the introducer, as described above. The expandability of the sheath also allows larger diameter devices to be inserted through the sheath since the sheath may expand to the diameter of the device during insertion.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the presen invention. It should also be realized by those skilled in the art that such equivalent constructions do not depart from the spirit and scop of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
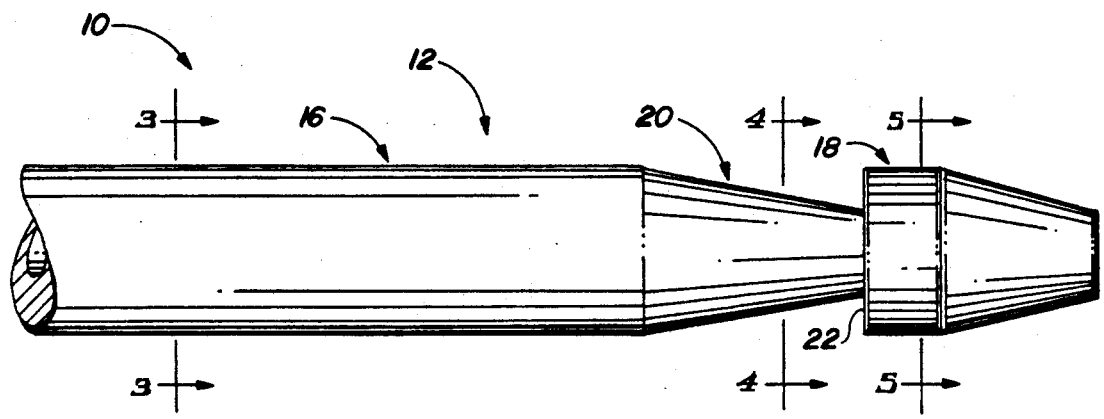
FIG. 1 is a partial plan view of the introducer of the invention illustrating it longitudinal body and head of the same diameter and its neck portion of a reduced diameter.
Figure 2:
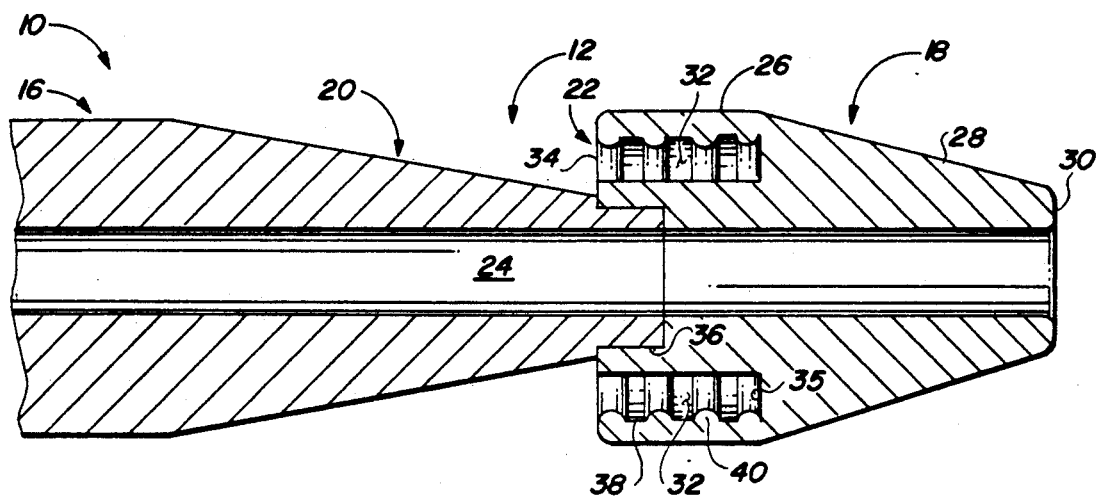
FIG. 2 is an enlarged cross-sectional view of FIG. 1 along lines 2—2 illustrating the cross-sectional configuration of the introducer including the annular slot formed longitudinally within the circumference of the head.
Figure 3:
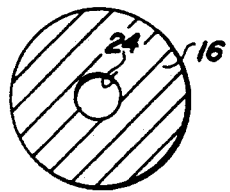
FIGS. 3, 4 and 5 are cross-sectional views of FIG. 1 along lines 3—3, 4—4 and 5—5, respectively, illustrating the transverse cross-sectional configurations of the introducer at its body portion, neck portion and head, respectively.
Figure 4:
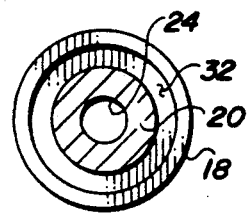
Figure 5:
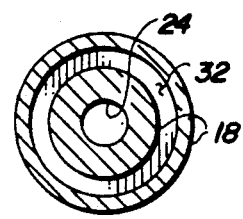

The sheath introducer 10 of the invention comprises an introducer 12 (see FIGS. 1 and 2) and a sheath 14 (see FIGS. 6-9). The introducer 12 of the invention comprises a generally cylindrical design having a body portion 16 and a head 18 of the same diameter joined together by a reduced diameter neck portion 20. The neck portion 20 preferably comprises a frusto-conical shape defining a vertical wall 22 at its juncture with the head 18. As best shown in FIG. 2, the body portion 16 and the neck portion 20 are preferably integrally formed together. The head 18 is rigidly secured to the distal end of the neck portion 20 by press fitting or the like. An axial guide wire hole 24 extends along the entire length of the introducer 12.

More particularly, the head 18 comprises a generally cylindrical rear portion 26 and a frusto-conically shaped portion 28 which forwardly converges with the axial guide wire hole 24, with the end 30 thus formed preferably rounded to eliminate sharp edges.

An annular blind slot 32 is formed circumferentially within the head 18, with its opened end 34 extending from the vertical wall 22. The blind slot 32 includes a bottom wall 35 and inner and outer concentric sidewalls 36 and 38. A thread 40 is formed on the outer sidewall 38. A similar thread (not shown) may also be formed on the inner sidewall 36 of the blind slot 32. As shown, all edges of the head 18 may be champhered or rounded.

Figures 6, 7:
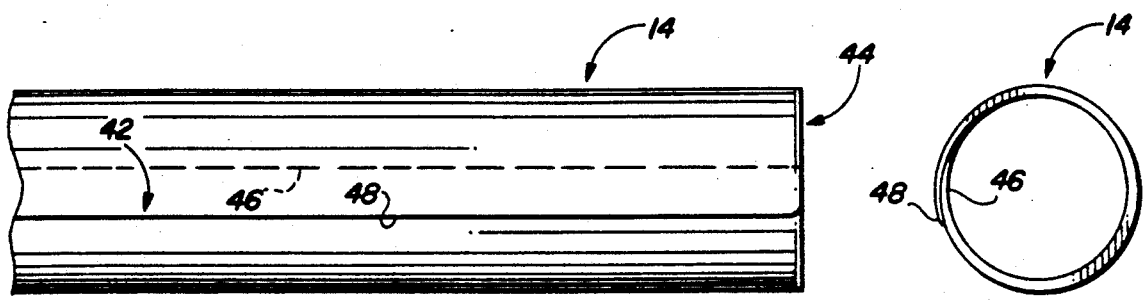
FIG. 6 is a plan view of the first embodiment of the sheath of the invention.
FIG. 7 is an end view of FIG. 6 illustrating the cylindrical design of the sheath and its overlapping longitudinal edges.

The first embodiment of the sheath 14 of the invention is illustrated in FIGS. 6 and 7 and includes a generally cylindrical design with longitudinal cut 42 formed from its tip 44 along a portion or along its entire length. The sheath 14 is formed with the longitudinal edges 46 and 48 defined by the longitudinal cut 42 positioned in an overlapping manner (see FIG. 7). The inner longitudinal edge 46 may be feathered to define a lumen which is cylindrical in shape and which includes a diameter allowing the sheath 14 to be slid over the introducer 12. It is noted that the overlapping of the longitudinal edges 46 and 48 may be achieved by producing the sheath 14 from a synthetic material or spring steel which includes a "memory" position to which the overlapping edges return to after compression or expansion.

Figures 8, 9:
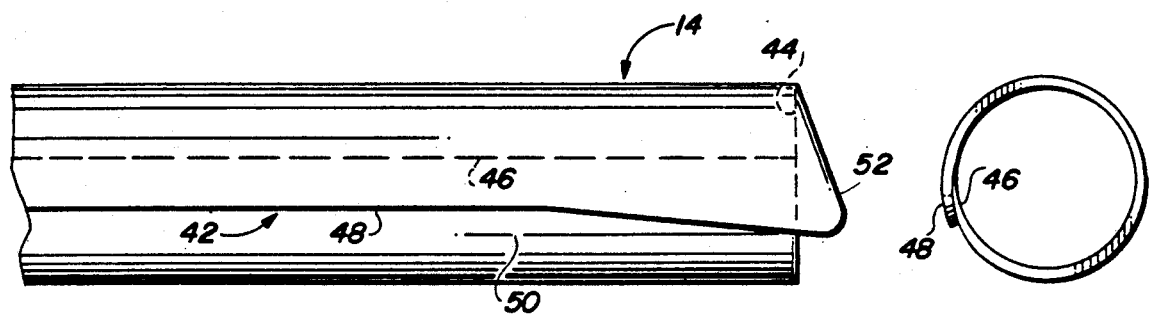
FIG. 8 is a plan view of the second embodiment of the sheath of the invention.
FIG. 9 is an end view of FIG. 8.

FIGS. 8 and 9 illustrate a second embodiment of the sheath 14 of the invention which is similar to the first embodiment described above, but having its outer longitudinal edge 48 extending appreciably from the tip 44 of the introducer 12 and extending rearwardly at an angle to a point 50 where the overlapping longitudinal edges 46 and 48 are parallel to each other as in the first embodiment. The distal corner of the outer longitudinal edge 48 thus forms a lip 52 which extends beyond the tip 44 of the sheath 14.

Other embodiments of the sheath introducer 10 of the invention are suggested. For example, the sheath may be manufactured from an elastomeric material having a large expansion coefficient that is temperature or chemical dependent. The sheath may then be manufactured in a cylindrical tube-like configuration similar to prior art sheath configurations. The head of the introducer may then include a larger diameter than its body or neck portions, sufficient to protect the tip of the sheath during insertion. Once inserted, the sheath may be exposed to a temperature increase or to the activating chemical, whereupon the sheath expands its lumen diameter allowing the head of the introducer to be withdrawn.

Figure 10:
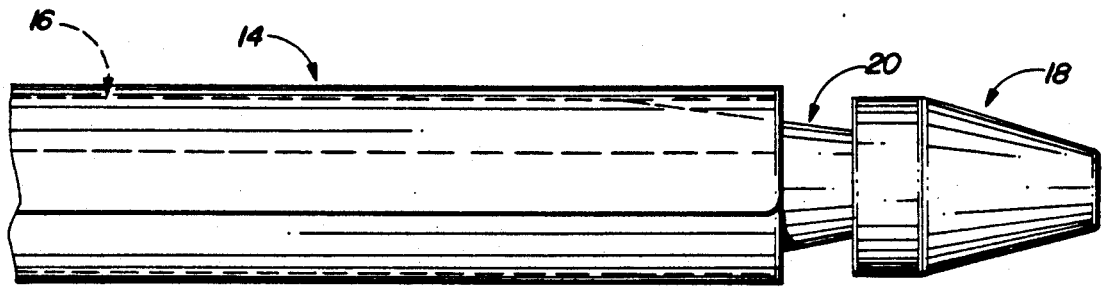
FIG. 10 is a plan view of the sheath introducer of the invention with the sheath partially inserted over the introducer.
Figure 11:
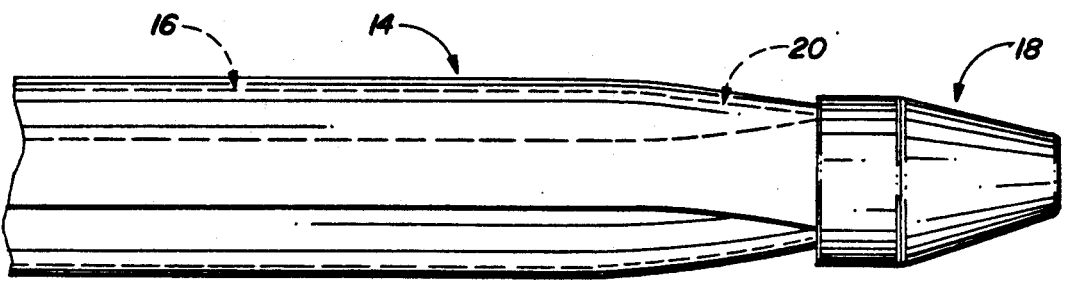
FIG. 11 is another plan view of the sheath introducer of the invention, partially cut away, with the tip of the sheath inserted within the annular slot formed within the head of the introducer.

FIGS. 10 and 11 illustrate the manner in which the sheath 14 is installed over the introducer 12. Firstly, the sheath 14 is inserted over the introducer 12 and slid along its length until the tip 44 of the sheath 14 is positioned about the neck portion 20 of the introducer 12. The tip 44 of the sheath 14 is then slightly compressed to reduce its diameter allowing the tip 44 to be inserted into the annular blind slot 32 as the sheath 14 is slightly advanced. It is noted that the lip 52 of the second embodiment of the sheath 14 facilitates insertion of the tip 44 into the annular blind slot 32 since the lip 52 acts somewhat as a guide. Once the tip 44 of the sheath 14 engages into the annular blind slot 32, the sheath 14 may be rotated clockwise to engag the thread 40 whereupon the sheath 14 is secured within the head 18 and protected from damage during insertion of the introducer 12.

After the introducer 12 is inserted into the arterial wall using the Seldinger or similar technique, the sheath 14 may be released from the head 18 of the introducer 12 by counter rotating the sheath 14 while pulling backwards until the tip 44 of the sheath 14 disengages from the annular blind slot 32 of the head 18. Once disengaged, the tip 44 of the sheath 14 returns to its cylindrical configuration because of its inherent memory. The head 18 of the introducer 12 is then allowed to pass through the sheath 14 as the introducer 12 is removed. It is noted that the expandability of the sheath 14 allows devices to be inserted through the sheath 14 into the arterial vein which include a diameter larger than the inner diameter of the sheath 14.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described,
What is claimed is:

1. A sheath introducer, comprising in combination:
an intruder including a body portion, a neck portion and a head, said body portion and said head comprising a substantially cylindrical design of substantially same diameter, said neck portion being positioned between said body portion and said head and including a diameter less than that of said head, said neck portion comprises a forwardly converging frusto-conical configuration defining a vertical wall between said neck portion and said head;
an expandable and contractible sheath, said sheath being configured and dimensioned to be slid over said body portion of said introducer at least up to said vertical wall and at least a distal tip of said sheath being contracted to be said in position, whereby said head protects said distal tip of said sheath from damage from said sheath introducer introduces said sheath into subcutaneous tissue and whereby said sheath may then be expanded to allow removal of said introducer leaving said sheath in the subcutaneous tissue; and
comprising an annular blind slot formed circumferentially therein having an opened end extending through said wall allowing said tip of said sheath to be contracted and positioned therein for protection from damage by said head.

2. The sheath introducer as set forth in claim 1, wherein said blind hole further comprises a thread for threaded engagement with said tip of said sheath.

3. The sheath introducer as set forth in claim 2, wherein said sheath comprises a substantially cylindrical design having a longitudinal cut formed along at least a portion thereof from said tip to define longitudinal edges, said sheath being composed of a material having a memory such that said sheath is expandable and contractible along the length of said longitudinal cut.

4. The sheath introducer as set forth in claim 3, wherein one of said edges protrudes beyond said tip to define a lip.

5. The sheath introducer as set forth in claim 4, wherein one said longitudinal edge overlaps the other.

6. The sheath introducer as set forth in claim 5, wherein said head includes a forwardly converging frusto-conical configuration.

7. The sheath introducer as set forth in claim 6, wherein said introducer comprises a longitudinal hole along its length for receiving an elongated guide member to guide the sheath introducer into place in the subcutaneous tissue.

8. A method for introducing a sheath into subcutaneous tissue, comprising the steps of:
inserting a hypodermic needle through the subcutaneous tissue into the desired location;
inserting an elongated guide member through said hypodermic needle into the desired location;
withdrawing the hypodermic needle leaving the guide member in the desired location;
concentrically positioning an expandable and contractible sheath over an introducer having a head frusto-conical shaped neck portion and a head and contracting a distal tip of the sheath about said frusto-conical shaped neck portion to be protected from damage by the head of the introducer, said step of contracting the distal tip of the sheath comprising inserting the tip into an annular blind slot positioned circumferentially within the head;
inserting a proximal end of the guide member into a longitudinal hole in the introducer and guiding the introducer and the sheath mounted thereon along the guide member into the desired location;
expanding the tip of the sheath allowing the head of the introducer to be withdrawn; and
withdrawing the introducer leaving the sheath in the desired location.

9. The method as set forth in claim 8, wherein the step of inserting the tip into the blind slot further comprises the step of twisting the sheath during insertion to threadably engage threads positioned within the blind slot to more rigidly secure the sheath about the introducer.

10. The method as set forth in claim 8 further comprising the step of withdrawing the guide member.

11. The method as set forth in claim 10, further comprising the step of inserting an instrument having a diameter greater than the lumen diameter of the sheath and during insertion, allowing the sheath to expand to permit passage of the instrument therethrough.

* * * * *

UNITED STATES PATENT AND TRADEMARK OFFICE
CERTIFICATE OF CORRECTION

PATENT NO. : 5,015,239
DATED : May 14, 1991
INVENTOR(S) : Kevin F. Browne

It is certified that error appears in the above—identified patent and that said Letters Patent is hereby corrected as shown below:

Column 5, line 63, please delete "intruder" and insert therefor --introducer--.

Column 6, line 8, please delete "said" and insert therefor --held--.

Column 6, line 10, after "damage", please delete "from" and insert therefor --when--.

Column 6, line 15, before "comprising", please insert --said head further--.

Signed and Sealed this

Eighth Day of September, 1992

Attest:

DOUGLAS B. COMER

*Attesting Officer*     *Acting Commissioner of Patents and Trademarks*